(12) United States Patent
Czerwinski et al.

(10) Patent No.: US 10,001,471 B2
(45) Date of Patent: Jun. 19, 2018

(54) IN VITRO TEST SYSTEM TO EVALUATE XENOBIOTICS AS IMMUNE-MODULATORS OF DRUG TRANSPORT AND METABOLISM IN HUMAN HEPATOCYTES

(71) Applicant: XENOTECH LLC, Lenexa, KS (US)

(72) Inventors: Maciej Czerwinski, Fairway, KS (US); David Benjamin Buckley, Olathe, KS (US); Faraz Kazmi, Overland Park, KS (US)

(73) Assignee: XENOTECH LLC, Lenexa, KS (US)

( * ) Notice: Subject to any disclaimer, the term of this patent is extended or adjusted under 35 U.S.C. 154(b) by 0 days. days.

(21) Appl. No.: 14/448,436

(22) Filed: Jul. 31, 2014

(65) Prior Publication Data
US 2014/0342944 A1 Nov. 20, 2014

Related U.S. Application Data

(62) Division of application No. 13/481,295, filed on May 25, 2012, now Pat. No. 8,846,576.

(60) Provisional application No. 61/490,931, filed on May 27, 2011.

(51) Int. Cl.
*G01N 33/50* (2006.01)

(52) U.S. Cl.
CPC ..... *G01N 33/5067* (2013.01); *G01N 33/5014* (2013.01); *G01N 33/5023* (2013.01); *G01N 2500/10* (2013.01)

(58) Field of Classification Search
CPC .................. G01N 33/5067; G01N 33/5014
USPC .......................................................... 506/23
See application file for complete search history.

(56) References Cited

U.S. PATENT DOCUMENTS

| | | | |
|---|---|---|---|
| 5,200,323 A | 4/1993 | Chang et al. | |
| 2004/0029153 A1 | 2/2004 | Takahashi et al. | |
| 2004/0043377 A1 | 3/2004 | Shimada et al. | |
| 2004/0241714 A1 | 12/2004 | Branch et al. | |
| 2005/0130254 A1 | 6/2005 | Park | |
| 2008/0064088 A1* | 3/2008 | Shuler .................. | C12M 23/16 435/293.1 |
| 2010/0040632 A1 | 2/2010 | Maini | |

OTHER PUBLICATIONS

Katial et al. (Clinical and Diagnostic Laboratory Immunology, Jan. 1998, pp. 78-81).*
Gebhardt et al., 2003, Drug Metabolism Reviews, 35(2-3), pp. 145-213.*
Tsujimoto et al. (Cryobiology, 72, 2016, pp. 78-81).*
Search Report and Written Opinion dated Dec. 26, 2012, in corresponding PCT/US2012/039657 filed on May 25, 2012.
Guoliang et al., "Effects of Plasma from Acute-on-Chronic Liver Failure Patients on Immortalized Human Hepatocytes in vitro," 2011, Hepato-Gastroenterology, 58:1328-1333.
Tukov et al., "Modeling Inflammation-Drug Interactions in vitro: A Rat Kupffer Cell-Helatocyte Coculture System", Toxicology in Vitro 20 (2006) 1488-1499.
Wilkening et al. "Comparison of Primary Human Hepatocytes and Hepatoma Cell Line HEPG2 with Regard to their Biotransformation Properties", Drug Metabolism and Disposition, 2003, vol. 31, No. 8, pp. 1035-1042.
Sunman et al., "Kupffer Cell Meiated IL2-Suppression of CYP3A Activity in Human Hepatocytes", Drug Metabolism and Disposition 2004, vol. 32, No. 3, pp. 359-363.
Hansel et al., "The Safety and Side-Effects of Monoclonal Antibodies", Apr. 2010, Nature Reviews: Drug Discovery, 9(4), pp. 325-338.
Jana et al., "Molecular Mechanisms of Cytochrome P450 Induction: Potential for Drug-Drug Interactions" 150(2004), pp. 97-114.
Lankveld et al., "In Vitro Testing for Direct Immunotoxicity: State of the Art", Immunotoxicity Testing: Methods and Protocols in Molecular Biology, vol. 598, Chapter 26, R.R. Dietert (ed), pp. 401-423.
Thurm et al., "Measurement of Cytokine Production Using Whole Blood," 2005, Current Protocols in Immunology, 7.18B.1-7.18B.12.
Dickmann et al., "Effects of Interleukin 6 (IL-6) and an anti-IL-6 Monoclonal Antibody on Drug Metabolizing Enzymes in Human Hepatocyte Culture," 2011, American Society for Pharmacology and Experimental Therapeutics, DMD Manuscript #38679, 38 pages.
Lee et al., "CYP-Mediated Therapeutic Protein-Drug Interactions: Clinical Findings, Proposed Mechanisms and Regulatory Implications," 2010, Clin Pharmacokinet, 49 (5), 295-310.
Kao et al., "Serum factors potentiate hypoxia-induced hepatotoxicity in vitro through increasing transforming growth factor-beta1 activation and release," 2009, Cytokine, Jul;47(1): 11-22.
D'Agosto et al., "CD81 expression on CD19+ peripheral blood lymphocytes is associated with chronic HCV disease and increased risk for HCV infection: a putative role for inflammatory cytokines," 2009, J. Biol Regul Homeost Agents, Jul-Sep;23(3): 155-64.
Vincent et al., "Inhibitory effect of the combination of CpG-induced cytokines with lamivudine against hepatitis B virus replication in vitro," 2009, Antivir Ther, 14(1): 131-5.
Bleau et al., "Interleukin-1beta, interleukin-6, tumour necrosis factor-alpha and interferon-gamma released by a viral infection and an aseptic inflammation reduce CYP1A1, 1A2 and 3A6 expression in rabbit hepatocytes," 2003, Eur J Pharmacol, Jul. 25;473(2-3): 197-206.
Liptrott et al., "The impact of cytokines on the expression of drug transporters, cytochrome P450 enzymes and chemokine receptors in human PBMC," 2009, Br J Pharmacol., 156(3): 497-508.

(Continued)

Primary Examiner — Karla A Dines
(74) Attorney, Agent, or Firm — Hovey Williams LLP

(57) ABSTRACT

A kit and method for evaluating in vitro the effect of a xenobiotic (e.g., a biologic drug) on drug metabolism in hepatocytes. The kit comprises a first culture of hepatocytes, a portion of in vitro xenobiotic-stimulated biological sample, and instructions for incubating the first culture of hepatocytes with the portion of in vitro xenobiotic-stimulated biological sample, and analyzing the activity, expression, or a combination thereof of a biomarker in the hepatocytes to evaluate the effect of the xenobiotic on drug metabolism in the hepatocytes.

12 Claims, 11 Drawing Sheets

(56) References Cited

OTHER PUBLICATIONS

Gorski et al., "In vivo effects of interleukin-10 on human cytochrome P450 activity," 2000, Clin Pharmacol Ther, 67(1): 32-43.

Diao et al., "Regulation of MRP2/ABCC2 and BSEP/ABCB11 Expression in Sandwich Cultured Human and Rat Hepatocytes Exposed to Inflammatory Cytokines TNF-a, IL-6, and IL-1beta," 2010, J Biol Chem, 285(41): 31185-31192.

Mao et al., "Predictions of Cytochrome P450-Mediated Drug-Drug Interactions Using Cryopreserved Human Hepatocytes: Comparison of Plasma and Protein-Free Media Incubation Conditions," 2012, Drug Metab Dispos, 40(4): 706-716.

Schmelzer et al., "Effect of Human Patient Plasma Ex Vivo Treatment on Gene Expression and Progenitor Cell Activation of Primary Human Liver Cells in Multi-Compartment 3D Perfusion Bioreactors for Extra-Corporeal Liver Support," 2009, Biotechnol Bioeng, 103(4): 817-27.

Lu et al, "Prediction of Pharmacokinetic Drug-Drug Interactions Using Human Hepatocyte Suspension in Plasma and Cytochrome P450 Phenotypic Data. III. In Vitro-in Vivo Correlation with Fluconazole," 2008, Drug Metab Dispos, 36(7): 1261-1266.

Wigmore et al., "Pro-inflammatory cytokine release and mediation of the acute phase protein response in fulminant hepatic failure," 1998, Intensive Care Med, 24, 224-229.

Maurel et al., "Primary Cultures of Human Hepatocytes: New Developments and New Applications", vol. 13, Supplement, 1998, pp. S68-S71.

Wigmore et al., "Down-Regulation of the Acute-Phase Response in Patients with Pancreatic Cancer Cachexia Receiving Oral Eicosapentaenoic Acid is Mediated via Suppression of Interleukin-6", Clinical Science, 1997, 92, pp. 215-221.

Andersson et al., "Down-Regulation of Cytokine Production and Interleukin-2 Receptor Expression by Pooled Human IgG", Immunology, 1993, 79, pp. 211-216.

Tateno et al., "Heterogeneity of Growth Potential of Adult Rat Hepatocytes In Vitro", Hepatology, Jan. 2000, pp. 65-74.

Pakala et al., "Eicosapentaenoic Acid and Docosahexaenoic Acid Block Serotonin-Induced Smooth Muscle Cell Proliferation", Arteriosclerosis, Thrombosis, and Vascular Biology, 1999, 19, pp. 2316-2322.

Suntharalingam, et al., "Cytokine Storm in a Phase 1 Trial of the Anti-CD28 Monoclonal Antibody TGN1412", N. Engl. J. Med., Sep. 7, 2006, vol. 355, issue 10, pp. 1018-1028.

Kasahara, et al., "Mononuclear Cell Adherence Induces Neutrophil Chemotactic Factor/Interleukin-8 Gene Expression", J. Leukocyte Biology, 1991, vol. 50, pp. 287-295.

* cited by examiner

IN VITRO TEST SYSTEM TO EVALUATE XENOBIOTICS AS IMMUNE-MODULATORS OF DRUG TRANSPORT AND METABOLISM IN HUMAN HEPATOCYTES

CROSS-REFERENCE TO RELATED APPLICATIONS

The present application is a divisional of U.S. patent application Ser. No. 13/481,295, filed May 25, 2012, which claims the priority benefit of U.S. Provisional Patent Application Ser. No. 61/490,931, filed May 27, 2011, entitled IN VITRO TEST SYSTEM TO EVALUATE XENOBIOTICS AS IMMUNE-MODULATORS OF DRUG TRANSPORT AND METABOLISM IN HUMAN HEPATOCYTES, each of which is incorporated by reference in its entirety herein.

BACKGROUND

Field of the Invention

The present disclosure relates to in vitro methods of evaluating xenobiotics and their effect on drug transport and metabolism.

Description of Related Art

There is an increasing number of biological drugs ("biologics") being developed as alternative therapeutics to traditional small molecule drugs. There are significant differences between these macromolecule biologics and small molecule drugs, including the ways in which they react with the body. Cytochrome P450 (CYP) enzymes are the major enzymes involved in small molecule drug metabolism and bioactivation. Several biologics are known to suppress CYP activity and result in small molecule drug toxicity following their administration. For example, influenza and flu vaccination has been shown to suppress CYP1A2 and CYP2C9 activity and thereby impair theophylline and warfarin clearance, respectively, resulting in theophylline and warfarin toxicity. The flu vaccine is also known to impair aminopyrine metabolism after inoculation. Some bacterial endotoxins (e.g., LPS) are known to affect the oral drug clearance of antipyrine, hexobarbital, and theophylline in otherwise healthy individuals. For example, following LPS treatment, changes in antipyrine (AP) clearance were found in humans and correlated with changes in TNF and IL-6.

SUMMARY

Since biologics affect drug metabolizing enzymes, which can change the systemic exposure to normally hepatically-cleared drugs leading to a loss of efficacy, drug toxicity, and/or exaggerated pharmacology, there is a need in the art for improved methods of evaluating potential drug-drug interactions, particularly in the pre-clinical setting and particularly between biologics and small molecule drugs. There is a further need for in vitro test systems that better reflect actual in vivo metabolism and potential interactions. An in vitro test system is described herein which allows assessment of xenobiotics as immune-mediated or direct modulators of liver function. Broadly, the test system includes a culture of a biological sample and a separate culture of hepatocytes. In the biological sample culture, the immune system cells respond to exposure to a xenobiotic by secreting signaling molecules such as cytokines, interleukins, interferons, and growth factors. The xenobiotic-stimulated fraction is separated and then transferred to the culture of hepatocytes. The immune system cell-mediated effects of xenobiotics on various biomarkers, such as drug transporters and drug-metabolizing enzymes are then measured in the hepatocytes. The method is particularly suited for determining and analyzing potential for (adverse) drug interactions, especially of biologics, when co-administered with traditional small molecule drugs.

A method of evaluating the effect of a xenobiotic on drug metabolism in hepatocytes is provided. The method comprises providing a first culture of hepatocytes, and providing a portion of a xenobiotic-stimulated biological sample. The portion of the xenobiotic-stimulated biological sample is transferred to the first culture of hepatocytes, and the activity and/or expression levels of a biomarker are analyzed in the hepatocytes. The term "biomarker" is used herein to refer to substances (such as peptides, molecules, proteins, etc.) that have predictive value for the effect of a given xenobiotic in a biological system. The term includes drug transporters, drug-metabolizing enzymes, or a combination thereof, and the like.

In related embodiments, a further method of evaluating xenobiotics as immune-modulators of drug transport and metabolism in hepatocytes is provided. The method comprises providing a first culture of a biological sample and a first culture of hepatocytes. The first biological sample culture is exposed to a xenobiotic for a period of time to yield a xenobiotic-stimulated biological sample. A portion of the xenobiotic-stimulated biological sample is transferred to the first culture of hepatocytes. The immune system-mediated effects of the xenobiotic on drug transporters and drug-metabolizing enzymes in the hepatocytes are evaluated by analyzing the activity and/or expression levels of a biomarker in the hepatocytes.

A kit for evaluating the effect of a xenobiotic on drug metabolism in hepatocytes is also provided. The kit comprises hepatocytes, a portion of a xenobiotic-stimulated biological sample, and instructions for incubating the hepatocytes with the portion of xenobiotic-stimulated biological sample and analyzing the activity and/or expression levels of a biomarker in the hepatocytes. In one or more embodiments the portion of a xenobiotic-stimulated biological sample is plasma comprising cytokines, which has been separated from xenobiotic-stimulated whole blood. In related embodiments, the portion of a xenobiotic-stimulated biological sample is a fraction comprising cytokines, which has been separated from xenobiotic-stimulated bone marrow.

A further method of evaluating the effect of a xenobiotic on drug metabolism in hepatocytes is also provided. The method comprises providing a first culture of hepatocytes and a xenobiotic-stimulated biological sample. The xenobiotic-stimulated biological sample is transferred to the first culture of hepatocytes, and the activity, expression, or combination thereof of a biomarker in said hepatocytes is analyzed. In some embodiments, the biological sample is isolated peripheral mononuclear blood cells.

DETAILED DESCRIPTION

Figure 1:
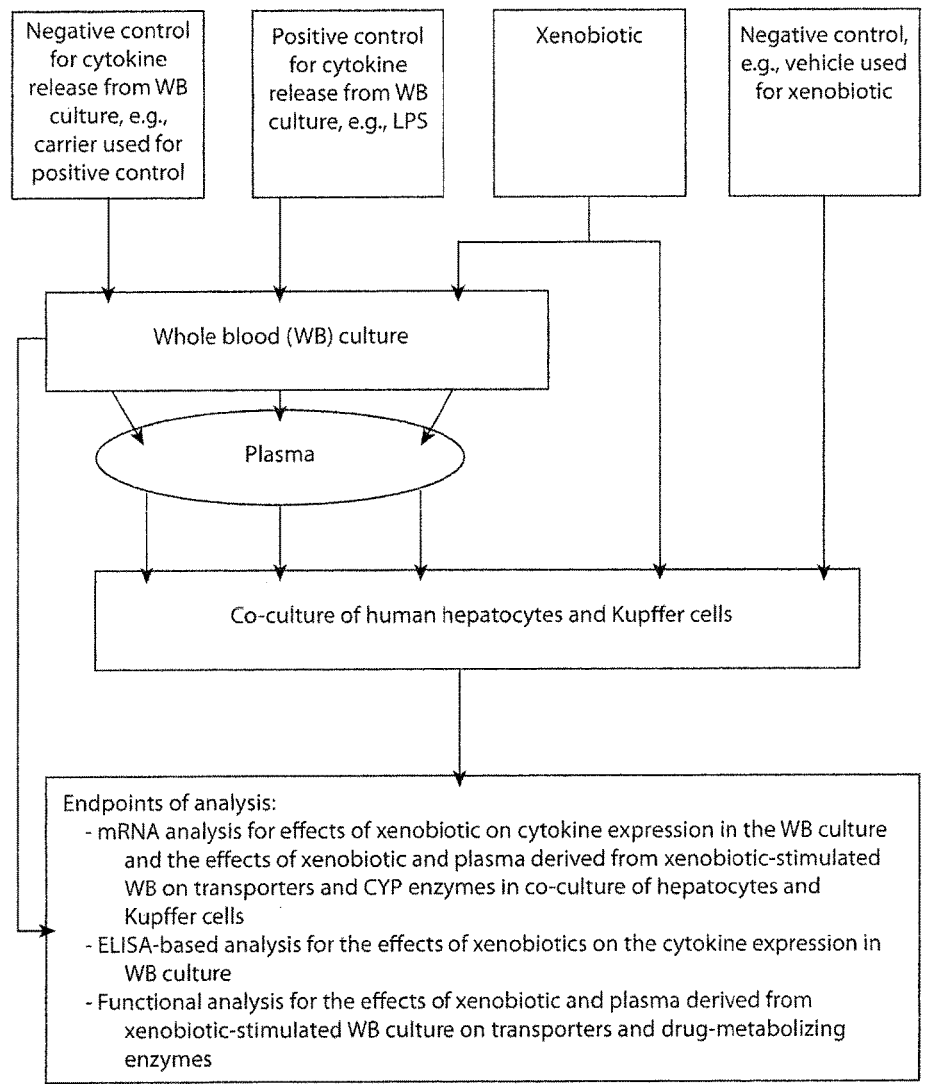
FIG. 1 is a flowchart of processes for the in vitro evaluation of xenobiotics as immune modulators of drug transport and metabolism in hepatocytes.

Embodiments disclosed herein are concerned with methods of evaluating xenobiotics as immune-modulators of drug transport and metabolism in hepatocytes. The term xenobiotics is used herein to refer to a compound that is foreign to a living organism, such as a drug. The term encompasses biologics as well as small molecule drugs, although the disclosed embodiments are particularly suited to biologic-type xenobiotics and certain small molecules that have pro-inflammatory cytokine effects. The term "biologics" is used herein to refer to therapeutic compounds (e.g., biologic medicines and drugs) that are created primarily through biological processes, rather than via pure chemical synthesis (like traditional small molecule drugs). Biologics can be composed of sugars, proteins, nucleic acids, or combinations thereof, and also include living cells and tissues. Biologics can be isolated from a variety of natural sources, such as human, animal, or microorganism. They can also be produced using recombinant DNA techniques. Exemplary biologics that can be evaluated using the present embodiments, include hormones (e.g., insulin), growth factors (e.g., erythropoeitin, GM-CSF, GH), cytokines (e.g., interferons, interleukins), receptors (e.g., soluble TNFα receptor), antibodies (e.g., anti-cytokine receptors, MAbs conjugated to small molecule drugs or poisons), enzymes (e.g., streptokinase), oligonucleotides (antisense) (e.g., fomivirsen for CMV retinitis), aptomers, iRNA or synthetic peptides, vaccines (e.g., influenza), biological extracts (e.g., bee venom), and the like.

The methods comprise providing a biological sample, which has been collected from a subject. In one or more embodiments, the subject is a mammal, including non-human mammals (e.g., rodents, dogs) and humans. In related embodiments, the subject is a human. In one or more embodiments, the sample can be from either a healthy (normal) or diseased subject. Exemplary biological samples include tissues which yield immune-mediated effects upon exposure to a xenobiotic, such as whole blood, bone marrow, and even isolated peripheral blood mononuclear cells (PBMCs). In one or more embodiment, the biological sample is whole blood. In use, a whole blood culture is prepared from at least a portion of the biological sample. In one or more embodiments, the culture comprises the collected whole blood and an anticoagulant (e.g., heparin, EDTA, sodium citrate) in a suitable container. In some embodiments, the culture does not include an anticoagulant (i.e., the whole blood is not mixed with an anticoagulant, and may, in some embodiments, be allowed to clot). Regardless, the whole blood culture is then incubated with a selected xenobiotic. In more detail, the xenobiotic is typically dispersed in a vehicle or carrier to produce a xenobiotic solution. Suitable vehicles or carriers will depend upon the xenobiotic, but can include saline, phosphate buffer, and the like. The concentration of the xenobiotic in the solution should be selected to be clinically relevant, which means that it closely approximate actual in vivo plasma concentrations, and will typically range from about 5% to about 2,000%, and more preferably from about 10% to about 1,000% of Cmax (the maximal concentration in plasma in vivo). The xenobiotic solution is then added to the whole blood culture. In one or more embodiments, the whole blood culture and xenobiotic are incubated for at least about 12 hours, and preferably from about 12 to about 48 hours, at a temperature of approximately 37° C., to yield stimulated whole blood. The immune system cells in the blood, such as PBMCs, are stimulated by the xenobiotic. In response, the cells produce signaling molecules such as growth factors, growth hormones chemokines, interferons, interleukins, (referred to collectively herein as "cytokines"), which are secreted or released into the plasma. In one or more embodiments, the methods described herein can be characterized as yielding artificially-stimulated blood (as opposed to natural in vivo stimulation) and related artificially-stimulated fractions.

The plasma is then separated from the xenobiotic-stimulated whole blood to yield xenobiotic-stimulated plasma. Any suitable separation technique can be used. In one or more embodiments, the xenobiotic-stimulated whole blood is centrifuged at about 600 x g for about 10 minutes. The supernatant (i.e., plasma) is then aspirated from the pellet. The xenobiotic-stimulated plasma can be analyzed directly or transferred to a second container and stored under suitable conditions until needed for analysis. In one or more embodiments, at least a portion of the xenobiotic-stimulated plasma is analyzed for the effects of the xenobiotic on the expression of cytokines. Typically, cytokines assayed in plasma from xenobiotic-stimulated whole blood cultures include, but are not limited to, interleukins IL-1B, IL-2, IL-6, IL-8, IL-10, and IL-12p70, granulocyte-macrophage colony-stimulating factor (GM-CSF), interferons (IFN-γ), tumor necrosis factor (TNF-α), and the like. In one or more embodiments, the plasma can be analyzed using an ELISA-based assay. Fluorescent or luminescent (e.g., chemiluminescent) probes can be used to detect the assay results. A portion of the whole blood can also be analyzed for the expression of cytokine genes by isolating cytokine mRNAs.

In the method, an aliquot (portion) of the xenobiotic-stimulated plasma is added to a culture of hepatocytes in a suitable cell culture medium (e.g., MCM+ (modified Chee's medium)). In one or more embodiments, the hepatocyte culture is actually a co-culture of hepatocytes and Kupffer cells (liver macrophages). The hepatocytes and/or Kupffer cells can be fresh or thawed (e.g., from cryopreserved cells), and isolated from human and/or animal livers. Pooled hepatocyte cultures prepared from multiple sources may also be used. A cell "source," as used herein, refers cells obtained from various donors, biopsies, tissue resections from different tissue samples or different tissue sources, different animals harboring cells (species), or primary, secondary, immortalized, or transformed cells. The cells may be derived from any mammalian source, including human, porcine, simian, canine, feline, bovine, equine, ovine, leporine, or murine sources, among others. In one or more embodiments, the hepatocytes are primary human hepatocytes. In related embodiments, the Kupffer cells are isolated from human livers. Cells may be obtained from a single source at two or more different times, combined, and cryopreserved. Such cells would still be considered to be prepared from a "single source." Cells from different sources include those obtained from mammalian cells of different genders, genotypes, ages, races (e.g., Caucasian, etc.), enzymatic or metabolic activities, species, or disease or health states (e.g., hepatocytes of hepatitis virus-infected liver, hepatocytes of HIV-1 infected liver, hepatocytes of healthy liver, hepatocytes of cigarette smokers, hepatocytes of individuals suffering from cirrhosis of the liver, or from other diseases or conditions, such as rheumatoid arthritis, cancer, and/or Crohn's disease, etc.). Cells from different sources are particularly desired for producing pooled preparations.

The terms "pooled" preparation or "pooling," as used herein, refer to a composition of cells that results from the combination of cells from more than one source, and generally comprises such cells suspended in a culture medium. The cells of such pooled preparations may be randomly selected, or may be specifically selected to provide the pooled preparation with a desired level of one or more metabolic activities (such as for example, a preparation of hepatocytes having a desired level of enzymatic activity, as described herein), or a desired cell characteristic (such as, for example, a preparation of hepatocytes derived from sources of a particular gender, genotype, age, race, or health state). For example, pooled hepatocyte preparations may be formulated so as to provide a preparation having the metabolic activities of an "average" hepatocyte sample or a preparation whose hepatocyte enzyme functions approximate the hepatocyte enzyme functions of freshly isolated hepatocytes. Such metabolic activities may include, for example, some or all of the following enzymatic activities: bupropion hydroxylase, amodiaquine N-dealkylase, diclofenac 4'-hydroxylase, coumarin 7-hydroxylase (COUM), dextromethorphan O-demethylase (DEX), 7-ethoxycoumarin O-deethylase (ECOD), mephenytoin 4-hydroxylase (MEPH), testosterone 6(β)-hydroxylase (TEST), tolbutamide 4-hydroxylase (TOLB), phenacetin O-deethylase (PHEN), chlorzoxazone 6-hydroxylase (CZX), or activities responsible for the phase II metabolism of 7-hydroxycoumarin (7-HCG (glucuronidase) and 7-HCS (sulfatase).

Those skilled in the art will recognize that hepatocyte-like cells may also be used in the disclosed embodiments. Hepatocyte-like cells include those derived from stem cells or an immortal cell line, that otherwise have enzymatic activity (see above) characteristic of hepatocytes as well as the ability to respond to cytokines (e.g., have appropriate functional receptors on their cells). Thus, the term hepatocyte is used herein to encompass such hepatocyte-like cells.

In some embodiments, the xenobiotic-stimulated plasma and hepatocyte culture are incubated for at least about 24 hours, and preferably from about 48 to about 72 hours at about 37° C. In one or more embodiments, the culture media and plasma is removed every 24 hours and replaced with fresh culture media and fresh stimulated plasma. It will be appreciated that exposure of the Kupffer cells to plasma containing cytokines may also result in their activation, causing the production and release of additional signaling molecules.

The cells in the hepatocyte culture are then analyzed to evaluate the immune system-mediated effects of the xenobiotic on biomarkers in the hepatocytes. More specifically, in one or more embodiments the cells in the hepatocyte culture are further incubated with a selected enzyme marker substrate. Exemplary marker substrates are listed in the table below.

TABLE I

| Enzyme | Marker substrate (reaction) |
| --- | --- |
| CYP1A2 | Phenacetin (O-dealkylation) |
| CYP2A6 | Coumarin (7-hydroxylation) |
| CYP2B6 | Bupropion (hydroxylation) |
| CYP2C8 | Amodiaquine (N-dealkylation) |
| CYP2C9 | Diclofenac (4'-hydroxylation) |
| CYP2C19 | S-Mephenytoin (4'-hydroxylation) |
| CYP2D6 | Dextromethorphan (O-demethylation) |
| CYP2E1 | Chlorzoxazone (6-hydroxylation) |
| CYP3A4/5 | Testosterone (6β-hydroxylation) |
| CYP3A4/5 | Midazolam (1'-hydroxylation) |
| UGT | 7-Hydroxycoumarin (glucuronidation) |
| SULT | 7-Hydroxycoumarin (sulfonation) |

In some embodiments, the hepatocyte culture is incubated in situ with the marker substrate for at least about 5 minutes (preferably from about 10 to 30 minutes) at about 37° C. The disappearance of substrate and/or appearance of metabolites can be analyzed using any suitable technique, including liquid chromatography with mass spectrometry (LC/MS), including tandem mass spectrometry (LC/MS/MS). Enzymatic activity can also be analyzed using microsomes isolated from the hepatocytes.

In one or more embodiments, the hepatocytes can be isolated from the culture to determine enzyme mRNA levels and activities or expression levels of drug metabolizing enzymes and drug transporters or other biomarkers after exposure to the xenobiotic-stimulated plasma. In related embodiments, total RNA can be isolated from the hepatocytes using known methods, such as TRIzol (Invitrogen) or TRI (Sigma-Aldrich), as well as column-based methods like RNAeasy (Qiagen) to determine the effect of the xenobiotic on the enzyme mRNA levels. Suitable RNA analysis techniques are known in the art, and include PCR (e.g., RT-PCR) techniques. In one or more embodiments, enzymatic activity assays (e.g., ELISA) can also be carried out to determine the activities of drug metabolizing enzymes and drug transporters. The test systems described herein are particularly suited for predicting the in vivo effect a xenobiotic may have on a particular enzymatic pathway known to be associated with a given small molecule drug. In this way, potential in vivo drug interactions can be predicted in the pre-clinical setting. Functional analysis can also be carried out on the hepatocytes to determine additional effects on the hepatocyte drug transporters and enzymes.

In one or more embodiments, the cells from the xenobiotic-stimulated plasma and hepatocyte culture can be incubated with a small molecule drug of interest. Depending upon the metabolic stability of the small molecule drug, the cells can be incubated with the drug for a time period of at least about 30 minutes, and typically from about 1 to about 4 hours. The metabolism of the small molecule drug by the hepatocytes (which may or may not have impaired enzymatic activity) can then be evaluated. This test system is particularly suited for studying potential biologic interactions with a small molecule having an unknown metabolism (i.e., where the specific enzymes and drug transporters involved in its metabolism are unknown or not well established). Again, the in vitro system provides a predictive model of in vivo metabolism and interaction.

It will be appreciated that the present methods can be applied to other tissues producing cytokines in vivo, such as bone marrow, as well as isolated PBMCs. The process will be the same for the whole blood described above, except that instead of separating plasma after incubation of the sample with the xenobiotic, the supernatant (which is the fraction containing the cytokines) will be collected. This xenobiotic-stimulated fraction will then be applied to the hepatocyte culture.

In some embodiments, the methods also further comprise appropriate positive and negative controls. In one or more embodiments, a positive control for cytokine release can be prepared using a known cytokine-eliciting compound to ensure that the biological sample is capable of producing an adequate or robust cytokine response and/or that this function has not been impaired. The method is almost identical to that described above for the xenobiotic, except that a compound with known cytokine-stimulating effects is used in lieu of the xenobiotic. Briefly, the biological sample is incubated with the selected compound. A portion of the sample (e.g., the plasma or other cytokine-containing fraction) is then separated, as described above, and incubated with a separate culture of hepatocytes (and/or Kupffer cells) following the same protocol used for the xenobiotic-stimulated whole blood and plasma. The resulting cells are also similarly analyzed. Exemplary compounds for use as the positive control include LPS, CpG DNA, PHA (phytohemagglutinin), Candida albicans soluble extract, zymosan, and the like. In some embodiments, where the xenobiotic is a conjugated protein, it may be desirable to also test each protein separately as a positive control or a negative control.

In one or more embodiments, a negative control for cytokine release can be prepared following substantially the same method described above. However, instead of incubating the biological sample with a xenobiotic, the sample is incubated with the selected vehicle or carrier (without any xenobiotic). A portion of the sample (e.g., the plasma) is then separated, as described above, and incubated with a separate culture of hepatocytes (and Kupffer cells) following the same protocol used for the xenobiotic-stimulated whole blood and plasma. The resulting cells are also similarly analyzed.

In one or more embodiments, a direct negative control can be prepared by incubating the culture of hepatocytes (and Kupffer cells) directly with the vehicle or carrier (without any blood, plasma, or xenobiotic). This process is followed by analysis of the cells using the same methods described above.

In further embodiments, a direct xenobiotic sample can be prepared by incubating the culture of hepatocytes (and Kupffer cells) directly with the xenobiotic (without any blood or plasma), followed by analysis of the cells using the same methods described above.

In yet further embodiments, an additional positive control can be prepared by incubating the culture of hepatocytes (and Kupffer cells) directly with a known hepatic enzyme suppressor, such as IL-6 (without any blood or plasma), followed by analysis of the cells using the same methods described above.

One of the benefits of the disclosed embodiments is the ability to evaluate multiple cytokines that are released in response to the xenobiotic in a single assay. This multiplexing allows not just the evaluation of multiple cytokines at once, but also assessment of potential differences in cytokine behavior in different cytokine combinations. More specifically, in prior art methods, cytokines that are released upon stimulation from a xenobiotic are not subsequently applied to hepatocytes. Rather, these cytokines are identified, and then synthesized or purchased from commercially-available sources. They are then examined, one at a time or in limited combinations, in drug metabolism studies. These processes do not evaluate or provide any information regarding the interaction between multiple cytokines and their effect on drug metabolism, as would be encountered in the in vivo system. Thus, current the CYP suppression by cytokines in current in vitro methods does not accurately reflect CYP suppression by cytokines in vivo. Thus, the present in vitro test systems provide a more realistic view of the in vivo effects of xenobiotics and drug interaction. The disclosed embodiments allow for an in vitro modeling of the interactions among hepatocytes and immune system cells in the peripheral blood and the liver upon xenobiotic exposure. The methods provide several benefits towards assessment of the effects of xenobiotics. These include the evaluation of the drug-drug interaction potential between small molecule drugs and biologic drugs that may be a consequence of a direct interaction by the xenobiotic with hepatocytes and Kupffer cells in vivo. Furthermore, xenobiotics that affect hepatocytes indirectly through the immune system cells in blood can also be evaluated. The disclosed methods assess the potential of xenobiotics, such as drug candidates, to cause drug-drug interaction by altering expression of drug-metabolizing enzymes and drug transporters. These data can streamline the process of pre-clinical drug development.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Analysis of Xenobiotic Effect on CYP Enzymes in Hepatocytes

Whole blood was collected from one healthy volunteer into vacutainers containing 15 USP sodium heparin/mL of blood. Blood cultures were stimulated ex vivo with lipopolysaccharides (LPS) 50 ng/mL in normal saline for 24 hrs at 37° C. Following the stimulation period, plasma was separated from the blood cells by centrifugation and stored at −80° C. Levels of cytokines IL-1B, IL-2, IL-6, IL-8, IL-10, IL-12p70, GM-CSF, INF-γ, TNF-α in the plasma from the LPS-stimulated whole blood were analyzed with the Sector Imager 24-00 and Pro-inflammatory 9-Plex kit manufactured by Meso Scale Discovery.

Figure 2:
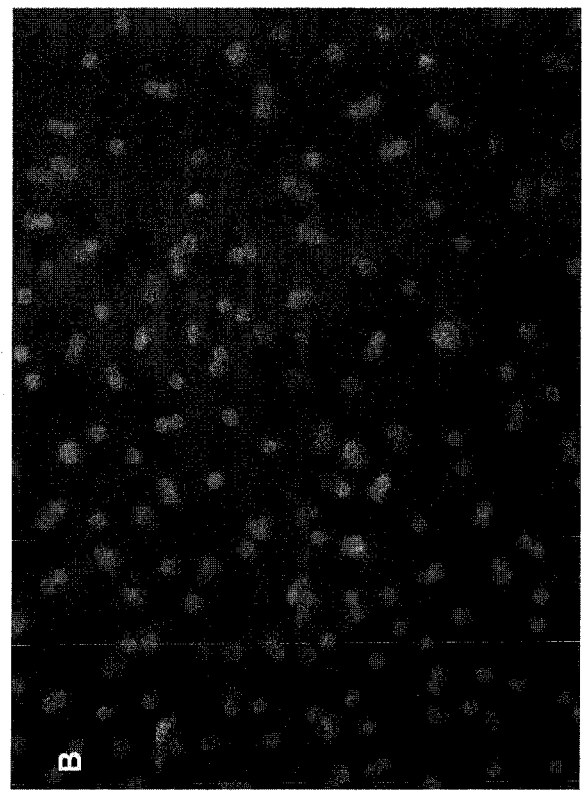
FIG. 2 shows fluorescent microscopy images of (A) Kupffer cells stained with anti-CD68 antibody; and (B) hepatocytes and Kupffer cells stained with a nuclear stain.
Figure 2:
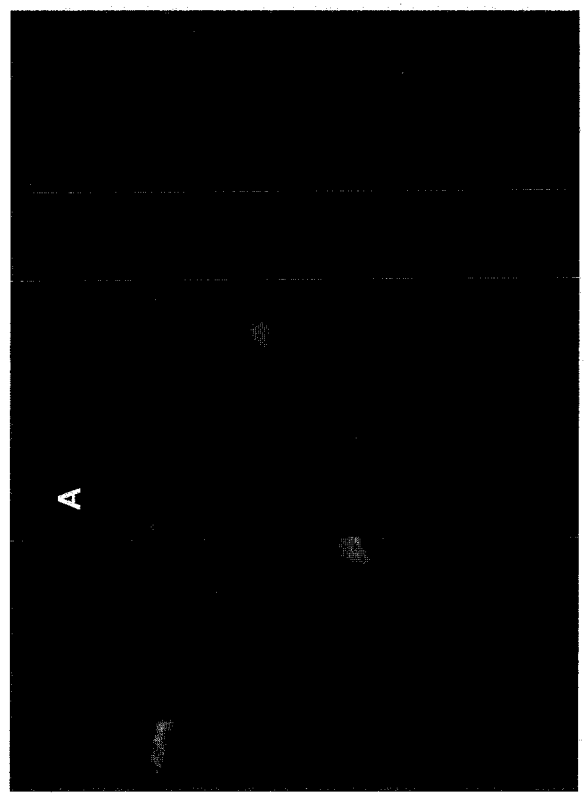

Co-cultures of primary human hepatocytes and Kupffer cells were prepared and stained with anti-CD68 mAb or a nuclear stain (4',6-diamidino-2-phenylindole, DAPI). Images were taken using fluorescence microscopy are shown in FIG. 2. The ratio of macrophage to hepatocyte was approximately 1:50.

Three concentrations (10, 20, or 50%) of LPS-stimulated plasma in a cell culture medium were prepared. Three concentrations (10, 20, or 50%) of plasma from saline-stimulated whole blood were prepared in a cell culture medium. Three concentrations (10, 25, or 50 ng/mL) of LPS in a cell culture medium were also prepared.

To assess effects of LPS on the expression of CYP enzymes in human hepatocytes, three co-cultures of human hepatocytes and Kupffer cells from three separate livers were treated daily for 72 hours with: (1) saline (negative control); (2) one each of the three concentrations of plasma from LPS-stimulated whole blood (positive control for cytokine release); (3) one each of the three concentrations of saline-stimulated plasma (negative control for cytokine release); (4) one each of three concentrations of LPS (direct xenobiotic test); or (5) interlukin-6 (10 ng/mL), a known suppressor of human CYP3A4 (additional positive control). After treatment, the cells in each group were incubated in situ with the appropriate marker substrates for the analysis of phenacetin O-dealkylation (marker for CYP1A2), bupropion hydroxylation (marker for CYP2B6) and testosterone 6β-hydroxylation (marker for CYP3A4/5) by LC/MS/MS. Following the in situ incubation, the same hepatocytes from the same treatment groups were harvested with TRIzol to isolate RNA, which was analyzed by qRT-PCR to assess the effect of the plasma from LPS-stimulated whole blood on CYP1A2, CYP2B6 and CYP3A4 mRNA levels.

Figure 3:
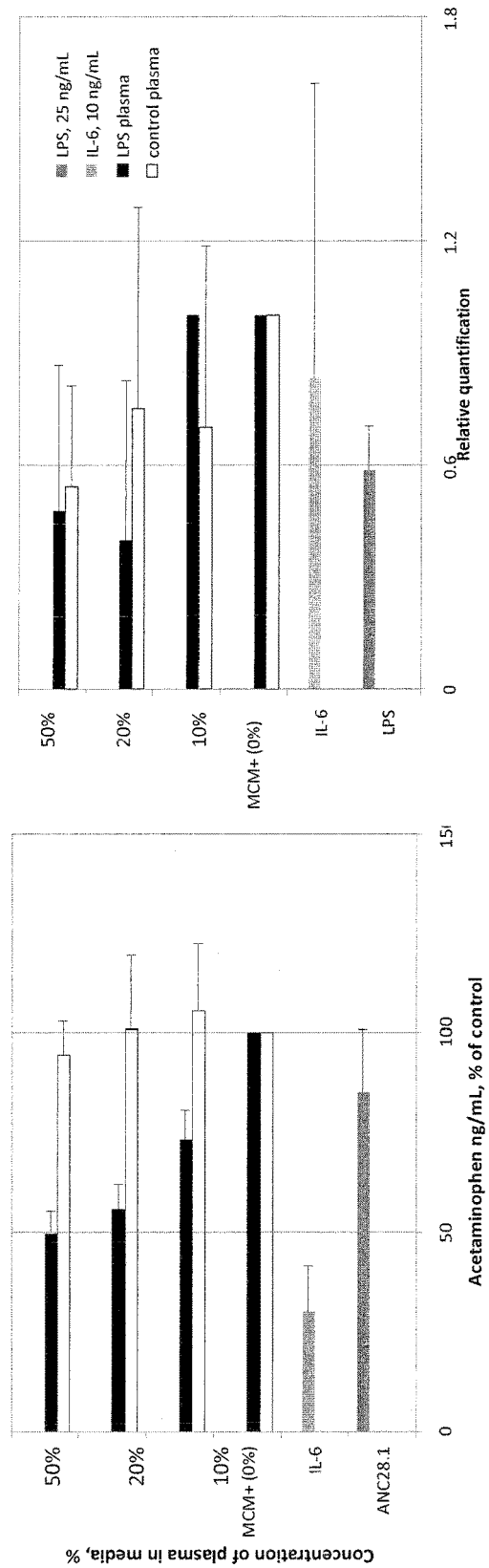
FIG. 3 shows graphs of the effects of plasma obtained from LPS- or control-stimulated whole blood on CYP1A2 in human hepatocytes (n=3) from Example 1.
Figure 4:
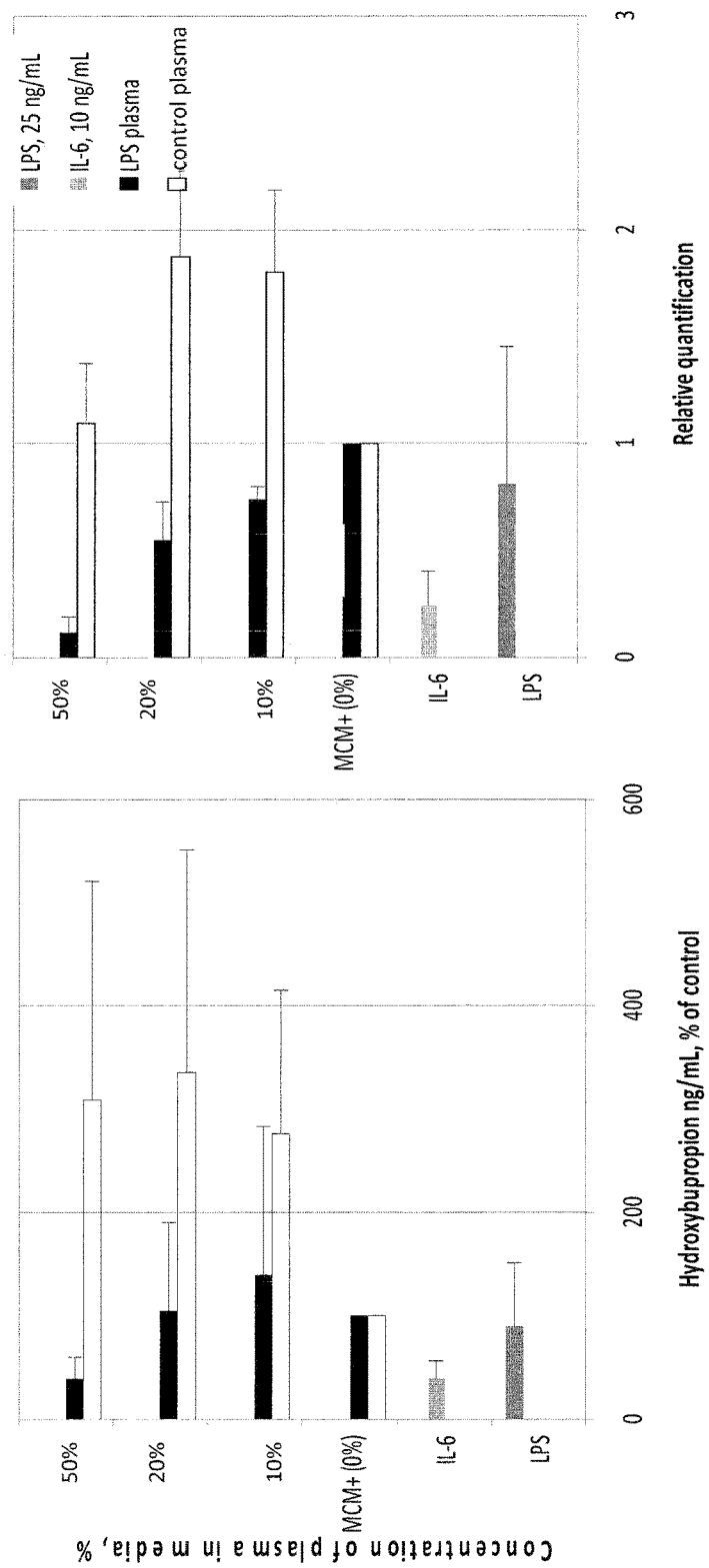
FIG. 4 shows graphs of the effects of plasma obtained from LPS- or control-stimulated whole blood on CYP2B6 in human hepatocytes (n=3) from Example 1.
Figure 5:
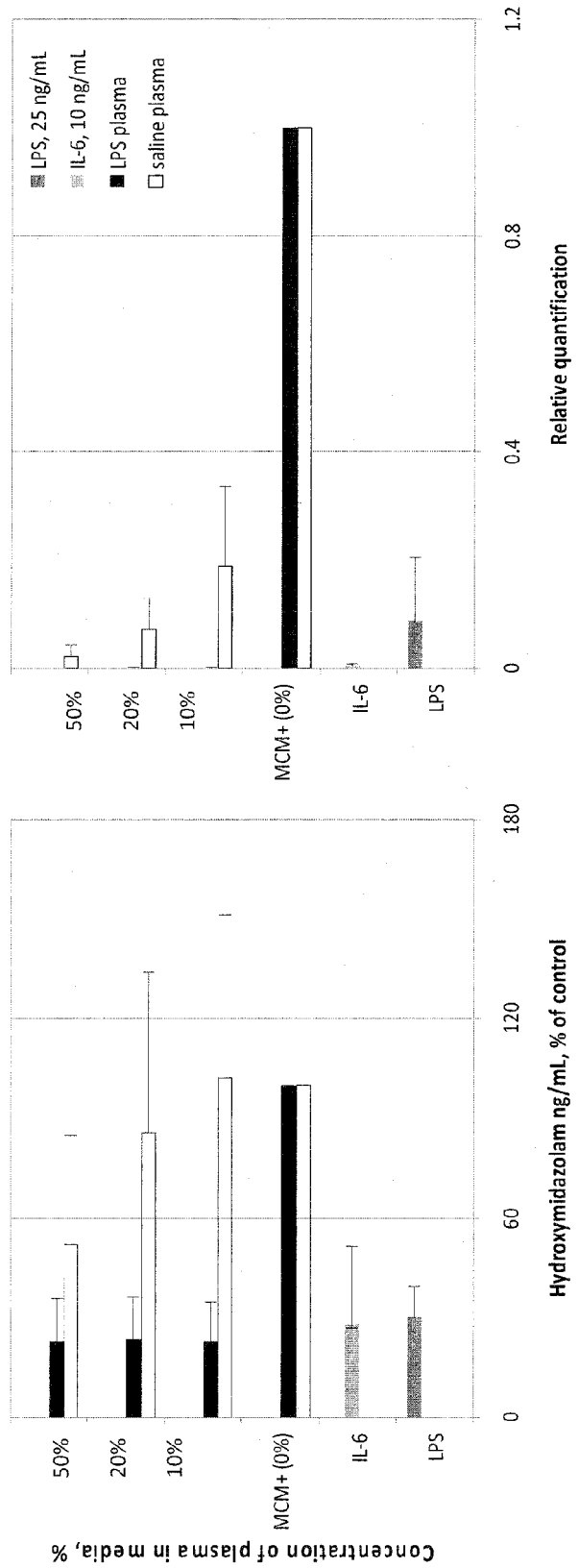
FIG. 5 shows graphs of the effects of plasma obtained from LPS- or control-stimulated whole blood on CYP3A4 in human hepatocytes (n=3) from Example 1.
Figure 6:
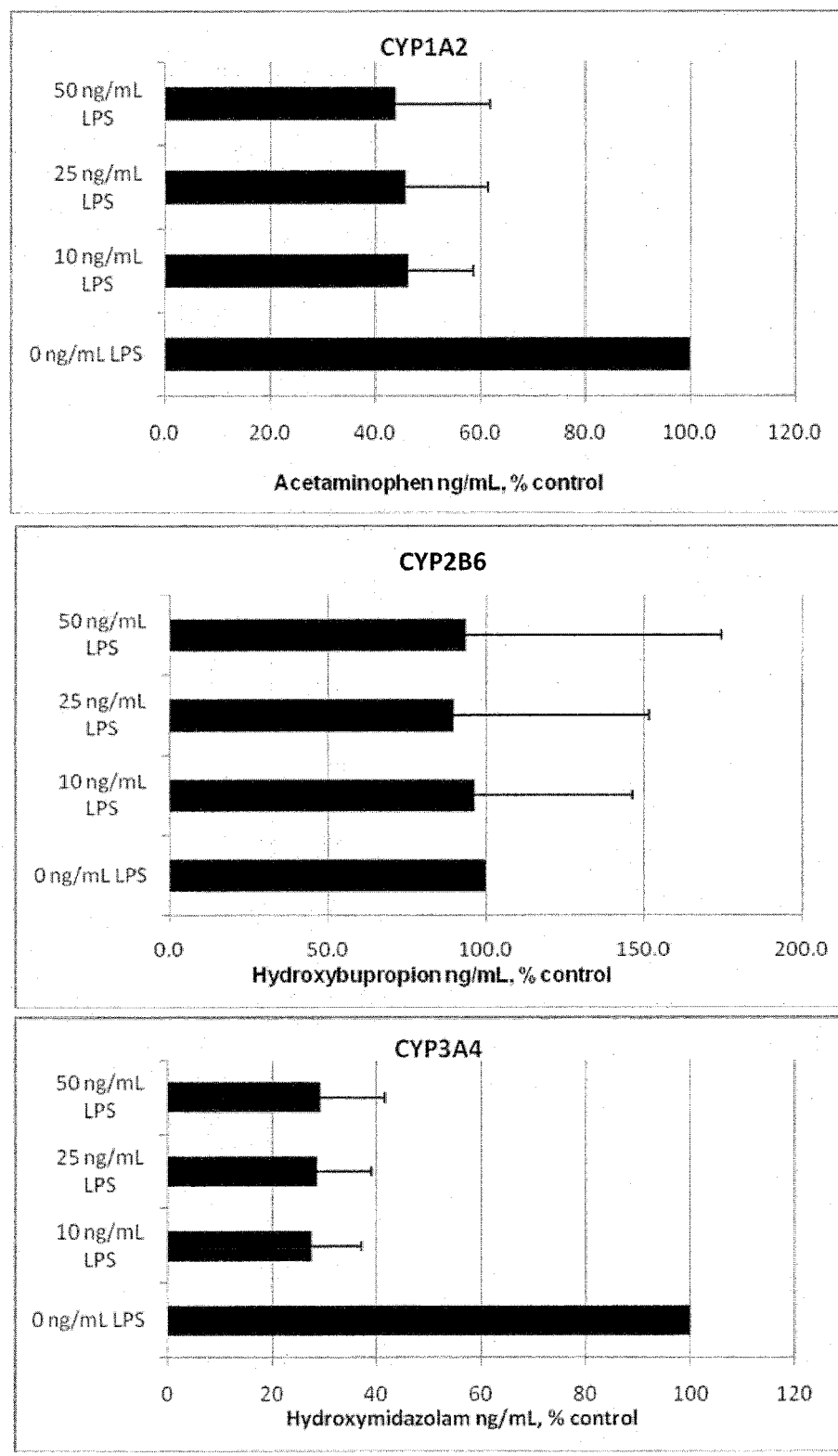
FIG. 6 shows graphs of the effects of LPS on CYP activity in human hepatocytes co-cultured with Kupffer cells (n=3) from Example 1.

Treatment of co-cultures of hepatocyte and Kupffer cells with IL-6 caused anticipated decreases in CYP1A2, CYP2B6, and CYP3A4 activity (FIGS. 3-5 and 8-10). Treatment of co-cultures of hepatocyte and Kupffer cells with plasma from LPS-stimulated WB caused a decrease in CYP 1A2, CYP2B6, and CYP3A4 activity (FIGS. 3-5). The effects of IL-6, LPS, and plasma from LPS-stimulated whole blood on enzymatic activities in hepatocytes were accompanied by expected corresponding changes in the levels of specific mRNAs. Taken together these results indicated that enzyme suppression rather than inhibition was the mechanism responsible for the observed changes in the activity of CYP enzymes (FIGS. 3-5). Treatment of co-cultures of hepatocyte and Kupffer cells with LPS caused decrease in CYP1A2 and CYP3A4, but not CYP2B6 activity (FIG. 6).

Under the conditions of this study where the IL-6 control caused anticipated decreases in CYP activities, treatment with up to 50% of plasma derived from LPS-stimulated WB resulted in comparable (CYP2B6 and CYP3A4) or greater (CYP1A2) decrease in the activity of CYP enzymes than the IL-6 control. These results indicate that if LPS is administered to a human patient, cytokines released from whole blood will affect drug metabolizing cells in the liver, meaning that the individual will have a reduced capacity for metabolizing other co-administered drugs (and a possibility for drug interaction).

The results demonstrate that the test system allows in vitro assessment of xenobiotics as immune-modulators of liver function.

Example 2

Monoclonal Antibody Xenobiotic

Figure 7:
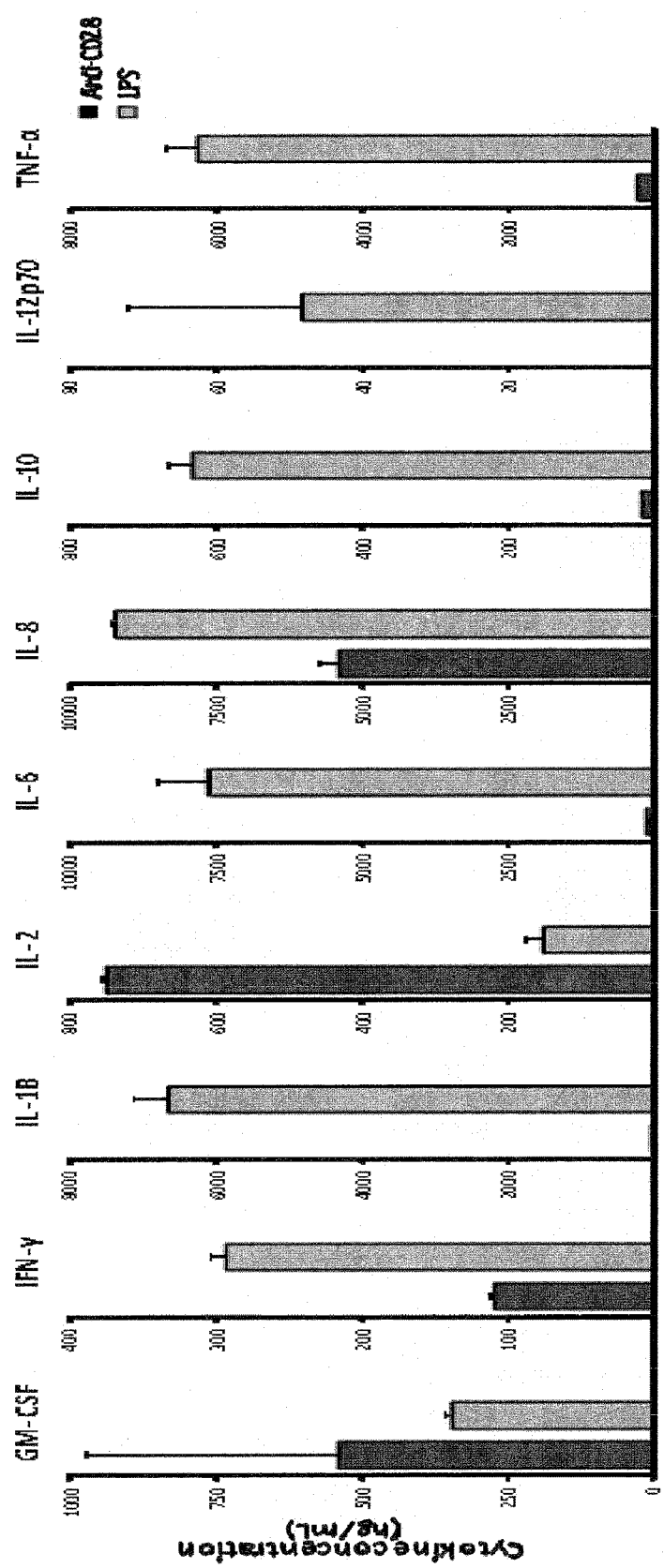
FIG. 7 shows graphs of the effects of anti-CD28 mAb and LPS on cytokine release in whole blood from Example 2.
Figure 8:
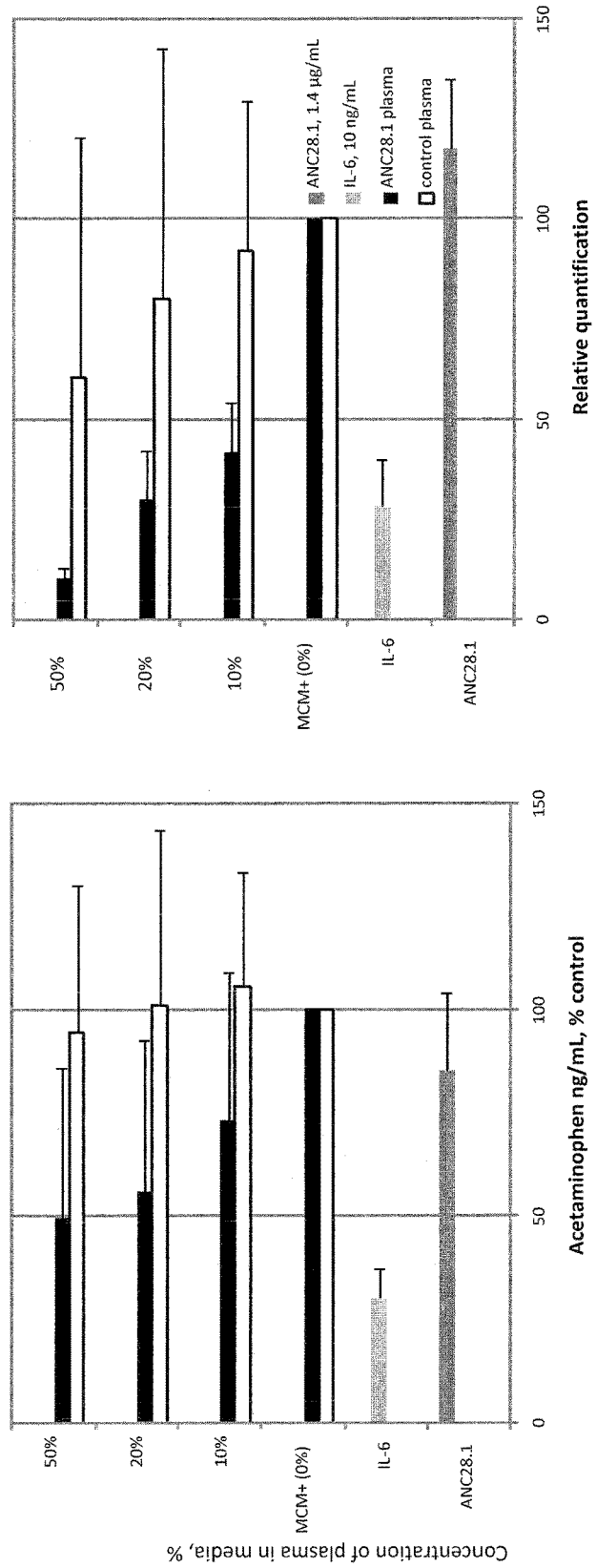
FIG. 8 shows graphs of the effects of plasma obtained from anti-CD28 antibody or control-stimulated whole blood on CYP1A2 in human hepatocytes (n=3) from Example 2.
Figure 9:
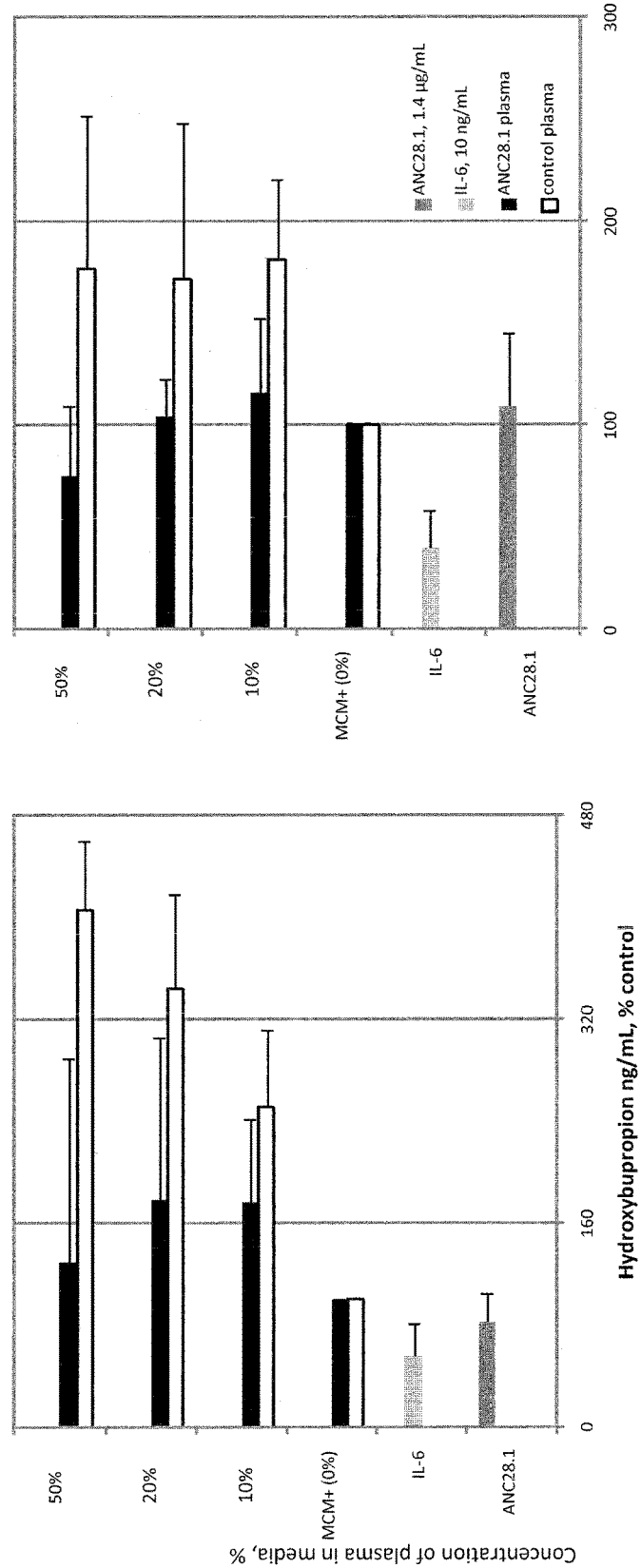
FIG. 9 shows graphs of the effects of plasma obtained from anti-CD28 antibody or control-stimulated whole blood on CYP2B6 in human hepatocytes (n=3) from Example 2.
Figure 10:
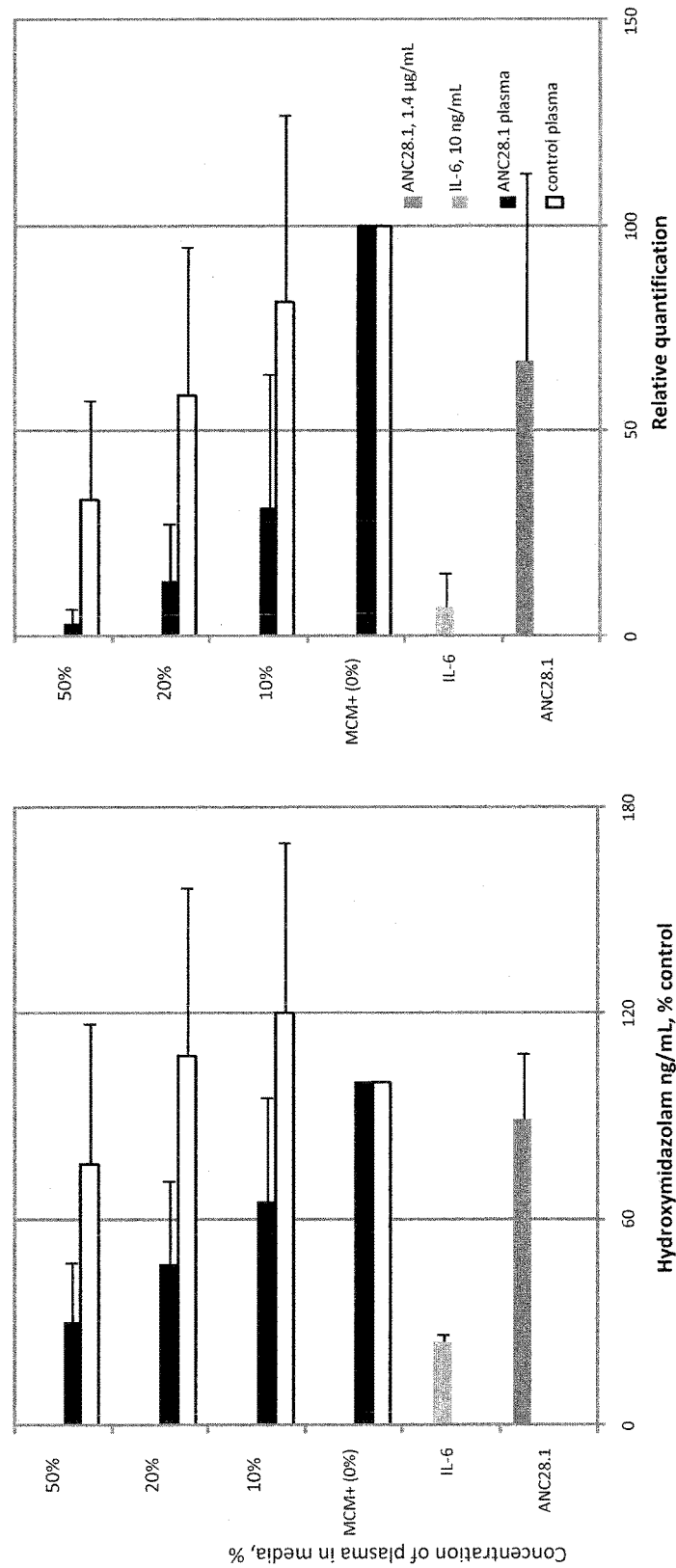
FIG. 10 shows graphs of the effects of plasma obtained from anti-CD28 antibody or control-stimulated whole blood on CYP3A4 in human hepatocytes (n=3) from Example 2.

In this Example, the same procedures used in Example 1 were followed, except that anti-CD28 antibody was used as the xenobiotic. LPS was also used as an additional positive control. The changes in pro-inflammatory cytokines observed upon treatment of whole blood with LPS or anti-CD28 antibody are illustrated in FIG. 7. Treatment of co-cultures of hepatocyte and Kupffer cells with plasma from anti-CD28 antibody-stimulated WB caused a decrease in CYP 1 A2, CYP2B6, and CYP3A4 activity (FIGS. 8-10). Treatment of co-cultures of hepatocyte and Kupffer cells with anti-CD28 antibody had little or no effect on CYP and CYP3A4, and CYP2B6 activity (FIGS. 8-10). The effects of IL-6, anti-CD28 antibody, and plasma from anti-CD28 antibody whole blood on enzymatic activities in hepatocytes were accompanied by expected corresponding changes in the levels of specific mRNAs. Taken together these results indicated that enzyme suppression rather than inhibition was the mechanism responsible for the observed changes in the activity of CYP enzymes (FIGS. 8-10).

Under the conditions of this study where the IL-6 control caused anticipated decreases in CYP activities, treatment with up to 50% of plasma derived from anti-CD28 antibody-stimulated whole blood resulted in comparable decrease in the activity of CYP enzymes as the IL-6 control. These results indicate that if anti-CD28 antibody is administered to a human patient, cytokines released from whole blood will affect drug metabolizing cells in the liver, meaning that the individual will have a reduced capacity for metabolizing other co-administered drugs (and a possibility for drug interaction).

Figure 11:
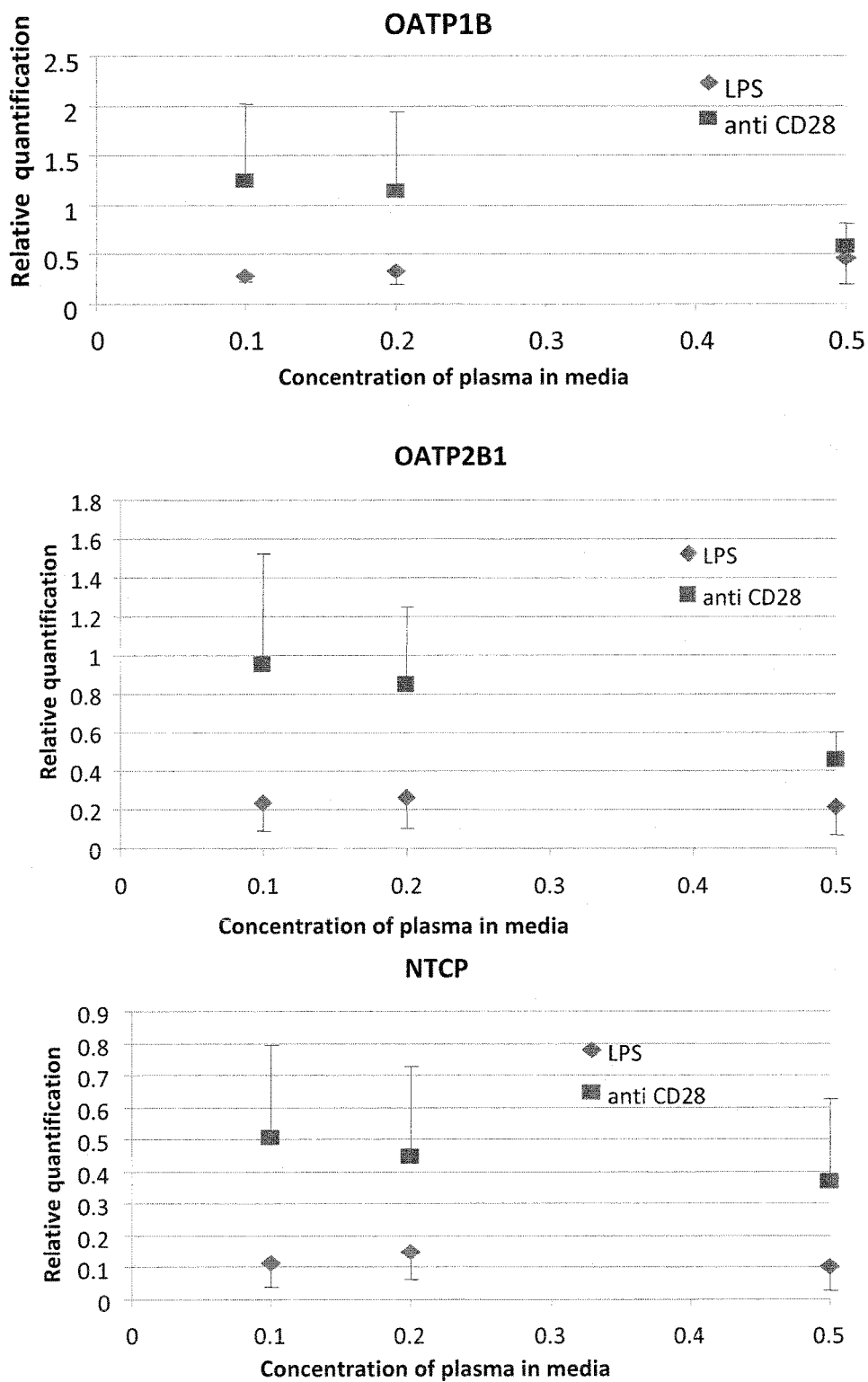
FIG. 11 shows graphs of the effects of plasma obtained from anti-CD28 antibody or control-stimulated whole blood on drug transporters in human hepatocytes (n=3) from Example 2.

The effects of treating hepatocytes with plasma from the LPS- or anti-CD28 antibody-treated whole blood resulted in decrease in the mRNA levels of hepatic transporters OATP1B1, OATP2B1 and NTCP (FIG. 11).

We claim:
1. A kit for evaluating in vitro the effect of a xenobiotic on drug metabolism in hepatocytes, said kit comprising:
   cryopreserved hepatocytes;
   an in vitro xenobiotic-stimulated biological sample, wherein said biological sample has been stimulated in vitro by said xenobiotic for about 12 to about 48 hours to yield said in vitro xenobiotic-stimulated biological sample, wherein said biological sample is selected from the group consisting of whole blood, bone marrow, and isolated peripheral blood mononuclear cells, wherein said xenobiotic is a small molecule or biologic drug; and instructions for incubating said hepatocytes with said in vitro xenobiotic-stimulated biological sample and analyzing the activity, expression, or a combination thereof of a biomarker in said hepatocytes to evaluate the effect of said xenobiotic on drug metabolism in said hepatocytes.

2. The kit of claim 1, wherein said cryopreserved hepatocytes further comprise Kupffer cells.

3. The kit of claim 1, wherein said hepatocytes are human hepatocytes.

4. The kit of claim 1, wherein said hepatocytes are pooled hepatocytes.

5. The kit of claim 4, wherein said pooled hepatocytes comprise a combination of cells from different genders, genotypes, ages, races, enzymatic or metabolic activities, species, or disease or health states.

6. The kit of claim 1, wherein said in vitro xenobiotic-stimulated biological sample is a portion of in vitro xenobiotic-stimulated biological sample prepared by exposing a first culture of said biological sample to said xenobiotic in vitro to yield a xenobiotic-stimulated biological sample, and separating said portion of said xenobiotic-stimulated biological sample.

7. The kit of claim 6, wherein said portion of in vitro xenobiotic-stimulated biological sample is plasma that has been separated from said in vitro xenobiotic-stimulated whole blood.

8. The kit of claim 6, wherein said portion of in vitro xenobiotic-stimulated biological sample is a cytokine-containing fraction that has been separated from said in vitro xenobiotic-stimulated bone marrow.

9. The kit of claim 6, wherein said portion of in vitro xenobiotic-stimulated biological sample is a cytokine-containing fraction that has been separated from said in vitro xenobiotic-stimulated peripheral blood mononuclear cells.

10. The kit of claim 1, wherein said xenobiotic is a biologic drug.

11. The kit of claim 10, wherein said biologic drug is selected from the group consisting of hormones, growth factors, cytokines, receptors, antibodies, enzymes, oligonucleotides, aptamers, synthetic peptides, and vaccines.

12. The kit of claim 1, wherein said in vitro xenobiotic-stimulated biological sample further comprises an anticoagulant.

* * * * *